(12) United States Patent
Cook

(10) Patent No.: US 6,862,550 B1
(45) Date of Patent: Mar. 1, 2005

(54) DETERMINING MEAT QUALITY OF A LIVE ANIMAL

(75) Inventor: Christian John Cook, Hamilton (NZ)

(73) Assignee: The Horticulture and Food Research Institute of New Zealand Limited, Palmerston North (NZ)

( * ) Notice: Subject to any disclaimer, the term of this patent is extended or adjusted under 35 U.S.C. 154(b) by 0 days.

(21) Appl. No.: 09/830,145

(22) PCT Filed: Oct. 26, 1999

(86) PCT No.: PCT/NZ99/00177

§ 371 (c)(1),
(2), (4) Date: Apr. 20, 2001

(87) PCT Pub. No.: WO00/25131

PCT Pub. Date: May 4, 2000

(30) Foreign Application Priority Data

Oct. 23, 1998 (NZ) ............................................. 332473

(51) Int. Cl.$^7$ ............................................. G06F 15/00
(52) U.S. Cl. ......................................... 702/136; 374/45
(58) Field of Search .................................. 119/174, 733; 600/518, 587, 437, 300, 549, 302; 702/136, 87; 374/45, 43; 514/15, 54, 634; 340/870.1; 452/68, 5; 700/90; 426/2; 73/597; 257/798

(56) References Cited

U.S. PATENT DOCUMENTS

| 3,070,773 A | 12/1962 | Woolston et al. |
| 3,661,142 A | 5/1972 | Flam |
| 3,781,837 A | 12/1973 | Anderson et al. |

(List continued on next page.)

FOREIGN PATENT DOCUMENTS

| DE | 3610960 A | 10/1987 |
| DE | 4025404 A | 2/1992 |
| EP | 166069 A | 1/1986 |
| GB | 2145224 A | 3/1985 |
| GB | 2251683 A | 7/1992 |
| WO | WO 95/01567 A | 1/1995 |

OTHER PUBLICATIONS

Garry B. Desroches, *Stress Affected Livestock as Seen by Thermography*, SPIE, vol. 934 Thermosense X (1988), pp. 120–136.

A.L. Schaefer et al, *Infrared Thermography of Pigs with Known Genotypes for Stress Susceptibility in Relation to Pork Quality*, Canadian Journal of Animal Science, vol. 69, Jun. 1989, pp. 491–495.

A.L. Schaefer et al, *Infrared thermography in three lines of pigs*. Canadian Journal of Animal Science, vol. 67, pp. 1181–1182, A.K. W (1987) (abstract).

A.L. Schaefer et al, *The effects of fasting and transport on acid–base balance, infrared heat loss and muscle quality of beef cattle*. Canadian Journal of Animal Science, vol. 67 p. 1182, B.C. (1987) (abstract).

(List continued on next page.)

*Primary Examiner*—John Bartow
*Assistant Examiner*—Xiuqin Sun
(74) *Attorney, Agent, or Firm*—Workman Nydegger

(57) ABSTRACT

A method of providing an indication of pH levels in an animal can alternatively be used to provide an indication of stress in an animal. Since pH and temperature are related to ultimate meat quality, the method of the invention may also be used to provide an indication of ultimate meat quality. In the method, periodic measurements are obtained corresponding to the body temperature of the animal. An algorithm is applied to the measurements obtained. The algorithm cumulatively takes account of variations of body temperature over time. The results of the algorithm are compared to a per-determined threshold. Alternatively, the results of the algorithm may be compared with a standard to provide a quantitative indication of pH, stress or meat tenderness. A system for providing an indication of meat quality/stress levels or pH levels in an animal is also provided.

47 Claims, 5 Drawing Sheets

U.S. PATENT DOCUMENTS

| | | | |
|---|---|---|---|
| 4,075,632 A | | 2/1978 | Baldwin et al. |
| 4,302,971 A | | 12/1981 | Luk |
| 4,854,328 A | | 8/1989 | Pollack |
| 4,865,044 A | * | 9/1989 | Wallace et al. ............. 600/549 |
| 5,050,612 A | * | 9/1991 | Matsumura ................. 600/483 |
| 5,458,418 A | * | 10/1995 | Jones et al. ................... 374/45 |
| 5,595,440 A | | 1/1997 | Gordin et al. |
| 5,595,444 A | * | 1/1997 | Tong et al. ................... 374/45 |
| 5,675,920 A | | 10/1997 | Long |
| 5,682,149 A | * | 10/1997 | Hofman ................. 340/870.17 |
| 6,704,595 B2 | * | 3/2004 | Bardy ........................ 600/518 |

OTHER PUBLICATIONS

C.J. Cook et al., *A conundrum of Biochemical and Physical Physiological Effects that Influence Meat Quality*, Agmardt Beef Industry R&D Conference, Palmerston North, New Zealand, 1990.

R.W. Purchas, *An Assessment of the Role of pH Differences in Determining the Relative Tenderness of meat from Bulls and Steers*, Meat Science, vol. 27, 1990, pp. 129–140.

A. Watanabe et al., *The Effects of the Ultimate pH of Meat on Tenderness Changes During Ageing*, Meat Science, vol. 42, No. 1, 1996, pp. 67–78.

L.H. Jacobson, et al, *The Effect of Pre–transport Cattle Management on Stress, Metabolism and Carcass Weight of Bulls*, $43^{rd}$ ICOMST, 1997, pp. 302–303.

L.H. Jacobson et al., *The Effect of Pre–transport On–farm Holding and Supplementary Feeding, On Welfare and Meat Characteristics of Bulls Subsequently Transported for Slaughter*, MIRINA Meat Research, Prepared for The New Zealand Meat Research and Development Council, Sep. 1996.

C.E. Devine et al., *High Ultimate pH in Sheep*, Proceedings of an Australian Workshop, Ed. S.U. Fabiansson, W.R. Shorthose and R.D. Warner AMLRDC, Sydney, Australia, pp. 55–65.

C.E. Devine et al., *The Effect of Growth Rate and Ultimate pH on Meat Quality of Lambs*, Meat Science, vol. 35, 1993, pp. 63–77.

C.E. Devine et al., *What is Meat Science*, Meat Science, in encyclopedia of Food Science and technology, ed, Hui, Y.H., WileyInterscience, John Wiley and Sons, Inc., New York, pp. 1708–1723.

* cited by examiner

DETERMINING MEAT QUALITY OF A LIVE ANIMAL

FIELD OF THE INVENTION

The present invention relates to methods and systems of using animal temperature measurements to predict meat pH and stress levels, as well as meat quality in an animal. Also provided are animal identification tags incorporating temperature sensors. These devices are also useful in monitoring the physiological state of an animal.

BACKGROUND ART

Livestock stress has long been recognised as having a major impact on the post-mortem quality of the animal tissue.[1,2,3,4,5]

It is well known that stress causes the depletion of an animal's energy reserves through depletion of glycogen in muscle tissue, and causes an increase in pH. pH values in excess of 5.8 result in poor meat quality. PH values in the range 5.8–6.1 cause toughness and furthermore, values in the range 5.8–7.00 cause increasing deterioration [A, B, C]. Qualities affected include:
Colour: the higher the ultimate pH the darker the meat colour. Customer demand is for bright red, rather than dark, meats;
Keeping ability: which decreases with the increase in pH;
Texture: high pHs tend to produce rubbery, watery meats; and
Tenderness: both high and low pH meats may be tender.

However, because of the other disadvantages associated with high pH, low pH tender meat is preferable. High pH, poor quality meats are not suitable for the export market and are often down-graded resulting in multi-million dollar losses to the primary meat sector each year.

Major causes of stress include rounding up and lairage of animals on the farm, crowded transport conditions, driving animals over long distances without rest, and handling procedures at processing plants, such as prodding and washing. It has also been recognised that by feeding an animal prior to slaughter, muscle energy reserves can be restored and down-grading avoided.[4] In ruminant animal such replenishment can take more than a day. In a monogastric, this is normally quicker. If a technology existed that could recognise at risk animals prior to processing then these animals could be treated.

U.S. Pat. No. 5,458,418, and U.S. Pat. No. 5,595,444 disclose methods of detecting poor meat quality in animals using infrared thermography. A single thermographic temperature measure is taken of an animal prior to slaughter. Animals with a thermograph outside a a predetermined test temperature range are rejected as likely to have meat of poor quality. Similarly, for a group of animals, animals showing a significant deviation in mean image temperature compared to the group mean temperature are rejected as likely to have meat of poor quality.

The infrared thermography methods disclosed in these patents are subject to a number of drawbacks. A one point temperature measurement prior to slaughter cannot reflect thermal history, nor accurately predict its effect on meat quality. The single reading may detect acute stress shortly prior to slaughter but not cumulative stress over a period of time. A further drawback is that an animal may be rejected for slaughter as a consequence of its mean image temperature in comparison with the group and not by reference to an absolute standard. Thus, animals may be unnecessarily downgraded. It is for this reason that infrared thermography has not performed well in practice as a predictor of meat quality.

It is an object of the present invention to provide a method for identifying stressed animals, or at least to provide the public with a useful choice.

The present applicant has found that in all animals subjected to stress, body temperature changes produce either an increase or decrease in skin heat loss. Changes in body temperature both up and down from the homeostatic norm are energetic that is energy must be used to re-establish norm by pulling body temperature up or lowering it (heat production or heat loss). Often these adjustments are quick and not reflected in deep body temperatures. They are, however, reflected in skin and surface temperatures and peripheral blood flow mechanisms ie. in the outer body. High energy expenditure can be made with little change seen in core temperatures. Falls in body/skin temperature are as (if not more) energetically demanding than rises.

In terms of stress measurement both a fall, or rise, in skin/body temperature can be an important indicator of stress, and such changes can be important both acutely and chronically (i.e. a number of changes) over time. In terms of predicting meat quality, cumulative stress, or more specifically cumulative energy expenditure, is more important than acute stress (other than extreme acute stress). A cumulative measure of skin/body temperature changes (both up and down) can provide an index over time of the amount of energy spent by the animal. The more energy spent by the animal over a 24 hour period prior to its slaughter the more likely that the meat will be of poor quality if the animal is not allowed an additional period to replenish its energy stores via eating.

As stress has energetic consequences it can influence production return and can have implications for animal welfare. A simple tool for measuring and offering quality control on these would be useful.

Animals that have meat ultimate pH levels in an acceptable range (pH 5.5–5.8) show a weak correlation between body temperature at slaughter and the actual meat pH. This correlation is greater if changes in body temperature are integrated over time, preferably for at least 12 hours prior to slaughter. A convenient way to do this is to use a cumulative variance around an averaged body temperature for an individual animal. Higher cumulative variances in temperature predict higher pH meat, a measure that relates to the amount of glycogen residing in the meat. Based on the applicant's findings of the correlation between pH, temperature and stress, it is proposed that animal sensor devices may be produced to monitor body temperature, and its variance, as a measure of an animal's stress level and as a predictor of meat quality.

Animal temperature sensors are known in the art. For example, in U.S. Pat. No. 3,781,837 and U.S. Pat. No. 4,865,044, tympanic temperature sensors are employed. In U.S. Pat. No. 4,854,328, a temperature sensor device is implanted at the base of an animal's skull. An ear tag component is provided which incorporates a unit for receiving signals from the implanted sensor, and indicating means responsive to the generated signal. In the case of U.S. Pat. No. 4,865,044, an ear tag is employed to contain the bulk of the temperature sensor circuitry, at a position remote from the tympanic animal temperature sensor.

The use of tympanic and surgically implanted sensor devices is usually contraindicated because of the high invasive load on the animal. Further, dislodgement problems are also encountered with tympanic sensors. Where implanted devices are used, incisions can easily become infected and the implantation procedure is more difficult to carry out.

Accordingly, it is a further object of at least a preferred embodiment of this invention to provide a temperature sensing device which overcomes some of these disadvantages, or again at least provides the public with a useful choice.

In a first aspect, the present invention may be broadly said to consist in a method of providing an indication of pH levels in an animal, the method comprising:
a) obtaining measurements corresponding to the body temperature of the animal at periodic time intervals;
b) applying an algorithm to the measurements obtained from a) which algorithm cumulatively takes account of variations in body temperature over time; and
c) comparing the results of the algorithm to a predetermined threshold or correlating the results of the algorithm with a pH standard.

One simple algorithm is to calculate cumulative temperature variance which may be calculated in a number of ways. A simple method discussed in greater detail below comprises:
a) measuring the animal's body temperature at intervals over a period of time;
b) determining that animal's average body temperature reading over that period of time;
c) calculating the variance between each temperature measurements taken under a) and the average determined in step b); and
d) adding all variance values calculated according to step c) to obtain the cumulative temperature variance score.

To calculate cumulative temperature variance at least two temperature readings must be taken. For accuracy, it is preferred that multiple readings of 10 or more are taken in a predetermined time period.

From our discussions above, the reader will appreciate that the pH level predicted is an indicator of meat quality, with a pH level greater than 5.8 indicating meat of poor quality.

In a further aspect, the present invention provides a method of providing an indication of stress levels in an animal, the method comprising:
a) obtaining measurements corresponding to the body temperature of the animal at periodic time intervals;
b) applying an algorithm to the measurements obtained from a) which algorithm cumulatively takes account of variations in body temperature over time; and
c) comparing the results of the algorithm to a predetermined threshold or correlating the results of the algorithm with a stress standard.

In another aspect, the present invention provides a method of measuring stress levels in an animal, the method comprising measuring the animal's pH level using a method of the invention, a pH level greater than 5.8 to 6.2 indicating a stressed animal.

In accordance with a further aspect of the present invention there is provided a method of providing an indication of meat quality in an animal, the method comprising:
a) obtaining measurements corresponding to the body temperature of the animal at periodic time intervals;
b) applying an algorithm to the measurements obtained from step a), which algorithm cumulatively takes account of variations in body temperature over time; and
c) comparing the results of the algorithm to a predetermined threshold or correlating the results of the algorithm with a meat tenderness standard.

By way of example, the New Zealand lamb AC & A standard may be used as a meat tenderness standard. Outputs from the algorithm may be pre-calibrated to the standard so that in use, the result from the algorithm may be compared with the standard to give an indication of meat tenderness.

In a specific form of the invention, the algorithm may calculate a mean of the measurements obtained in step (a); calculate a variance of each measurement from the calculated mean; and integrate the variances over time. In one preferred form of this embodiment, the measurements may be taken for a predetermined time period and a final mean calculated at the end of that predetermined time period. The integration of the variances will then be conducted over the predetermined time period. In an alternative version of this simple algorithm based on variances from a mean temperature, a running mean may be progressively determined from the measurements obtained in step (a). At each stage, the variation of the temperature measurement from the previous calculated running mean may be integrated over time. This reduces the memory requirements of the device to implement the method.

More sophisticated algorithms may be employed which depart from the simple method of calculating the variances from the mean. These more sophisticated algorithms may determine a cumulative value which is dependent on progressive changes or trends in the measurements obtained from step (a), rather than being dependent on absolute temperature measurements. This avoids the need to calibrate the temperature sensors.

Thus the measurements obtained from step (a) may or may not be actual temperature measurements. For example, in any embodiment utilising absolute temperature values, relatively inexpensive thermistors may be employed to obtain the temperature measurements with the circuitry in which the thermistors are employed compensating for any variation in the measured temperature from the real temperature. This calibration may be effected by calculating a correction coefficient and programming this into a microprocessor employed in the circuit.

In more sophisticated algorithms which rely on temperature changes rather than absolute values, no calibration may be required.

The body temperature is preferably measured on the outer part of the animal since temperature adjustments to accommodate stress appear to be more pronounced on the outer part of the animal compound to core temperatures. In a most preferred form of the invention, the skin measurements may be taken e.g. on the ear of the animal.

In any embodiment in which the outer body temperature is determined on the skin, a correction for the effects of ambient temperature will be required. This can be achieved through the use of an ambient temperature sensor. Additionally, correction for solar radiation may also be required where the skin temperature sensor is exposed to sunlight. The body temperature may also be measured in more internal locations such as the inner ear. This may avoid the requirement for ambient temperature compensation. However stress induced temperature fluctuation may be less and more sensitive temperature measuring devices may be required when measuring in this position.

In the simplest of embodiments where the algorithm is applied at the end of the predetermined time period, a device implementing the method may be provided with an indicator to indicate the results of the comparison step conducted in step (c). If the failure of step (c) is indicated by way of a flashing light or audible alarm then the same facility may be used to periodically indicate the correct functioning of the device. For example, where a frequently flashing light indicates failure of step (c), an intermittent flashing of the same light may merely indicate that the device is functioning. A non flashing light will thus indicate to an attendant that the device has malfunctioned or has lost power.

In the embodiment where the algorithm is progressively employed to the measurements obtained in step (a), step (c) may be employed after each implementation of the algorithm. Thus, if the animal fails the test at any point throughout a predetermined time period then an indicator may be employed to show that the animal has failed the test. The method may then be reemployed starting at the beginning of the predetermined time period. If at any time during the retest the animal fails step (c) again then the same indicator will indicate failure of the test and the process will be repeated. However, should the animal progress to the end of the predetermined time period without failing step (c) then an alternative indication may be given that the animal has passed the test for the full duration of the predetermined time period and thus is fit for slaughter. Suitably once the animal has reached this point it should be slaughtered without further delay and without the opportunity for the animal to incur further stress.

In one specific implementation of the method, it may not be necessary to wait for the full duration of a specific predetermined time period if the time period from rounding up to delivery of the animals to the abattoir is less than the predetermined time period. In the method which progressively applies the algorithm, if the animal has not yet failed the test during the time thus far and if the conditions before the testing started were such that the animals were unlikely to be subjected to stress, then the animals might proceed to immediate slaughter.

In accordance with another aspect of the present invention, there is provided a system for providing an indication of meat quality in an animal to be slaughtered, the system including:
 a body mountable measurement device for obtaining measurements corresponding to the body temperature of the animal at periodic time intervals over a period of 3–36 hours;
 a processor having an input means to receive the measurements from the measurement device, the processor operable to implement an algorithm to the measurements, which algorithm cumulatively takes account of variations in body temperature over time, wherein the processor has an output means for the result of the algorithm.

The system may be implemented in an all-in-one indicator device. Such a device may be mounted on the animal eg ear tag, tail tag or provided on a collar. The tag may also incorporate the measurement device. In an alternative form of the invention, the measurement device may be remote from the tag. The measurements may be sent to the processor by way of a transmitter or by a cable. In one preferred form of the invention, the measurement device may be provided by way of a thermistor to be deposited in the inner ear canal of the animal with a cable connected to an ear tag which houses the processor.

In yet another embodiment of the present invention, the processor may be provided by way of a remote computer. In this embodiment, a device for mounting on the animal will suitably incorporate transmitters to send the measurements to the remote computer. The remote computer may be a field device which is able to sense and account for ambient temperatures and solar radiation. Alternatively, a separate field device may be provided to send information relating to ambient temperature and solar radiation to a remote processor. The remote computer also receives the measurements from the measurement device provided on the animal either directly or via the field device.

The output from the processor may be in any of various forms. A simple numeric value may be output for the attendant to decide whether or not it falls within acceptable limits. The value might be compared to a meat tenderness scale for quantitve assessment as to whether it falls within acceptable limits. However, in most embodiments it is preferred that the processor is operable to compare the outputs of the algorithm to a predetermined threshold. The system may also include an indicator to indicate where the output of the algorithm has exceeded the predetermined threshold. Any of the features described in connection with the above-described method of indicating meat quality may be implemented in the system.

In accordance with yet another aspect of the present invention, there is provided a system for indicating cumulative stress in an animal, the system including:
 a body mountable measurement device for obtaining measurements corresponding to outer body temperature of the animal at periodic time intervals over a period of 3–36 hours:
 a processor having an input to receive measurements from the measurement device, the processor operable to implement an algorithm to the measurements, which algorithm cumulatively takes account of variations in body temperature over time, wherein the processor has an output for the result of the algorithm.

The system for providing an indication of stress may be implemented in any of the various forms discussed above for the system providing an indication of meat quality. Such a system for indicating cumulative stress might have particular application to animals where the effects of stress might be dangerous either to the animal itself, to other animals or in particular to humans. For example, horses might be more prone to erratic behaviour and a danger to their riders if they are subjected to sustained periods of stress. A system implemented in the form of an all-in-one indicator device may provide simple indication to the rider that the animal is stressed and needing rest or food.

Preferably, the processor is also operable to compare the output of the processor with a predetermined threshold. The system preferably incorporates an indicator to provide indication that the predetermined threshold has been exceeded. In an all-in-one indicator device, this may be implemented by a simple visual indicator such as a flashing led. In an embodiment with a remote computer then the output of the computer may provide the identification numbers of those animals which have exceeded the threshold.

In accordance with a still further aspect of the invention, there is provided a system of providing an indication of ultimate meat pH of an animal, the system including:
 a body mountable measurement device for obtaining measurements corresponding to outer body temperature of the animal at periodic time intervals over a period of 3–36 hours:
 a processor having an input to receive measurements from the measurement device, the processor operable to implement an algorithm to the measurements, which algorithm cumulatively takes account of variations in body temperature over time, wherein the processor has an output for the result of the algorithm.

In a further aspect, the present invention provides:
A temperature sensing device including:
 a tag having an attachment portion to extend through a body part of an animal, the tag incorporating an indicator means; and one or more animal temperature sensors disposed on/in the attachment portion for contact with the animal during use.

Preferably, the tag is an ear tag. Preferably, an ambient temperature sensor is also provided 100 on the tag. Further, the tag may be provided with comparison means to compare the ambient temperature with the animal temperature. An indicator may also be disposed on the tag, the indicator being responsive to the comparison means.

Desirably, the tag comprises a one piece moulded body.

Also contemplated by the present invention is the use of the temperature sensing device in the methods of the invention as described above.

This invention may also be said broadly to consist in the parts, elements and features referred to or indicated in the specification of the application, individually or collectively, and any or all combinations of any two or more of said parts, elements or features, and where specific integers are mentioned herein which have known equivalents in the art to which this invention relates, such known equivalents are deemed to be incorporated herein as if individually set forth.

The invention consists in the foregoing and also envisages constructions of which the following give examples.

BRIEF DESCRIPTION OF THE DRAWINGS

The present invention will now be described with reference to the accompanying drawings in which.

DETAILED DESCRIPTION

Figure 1:
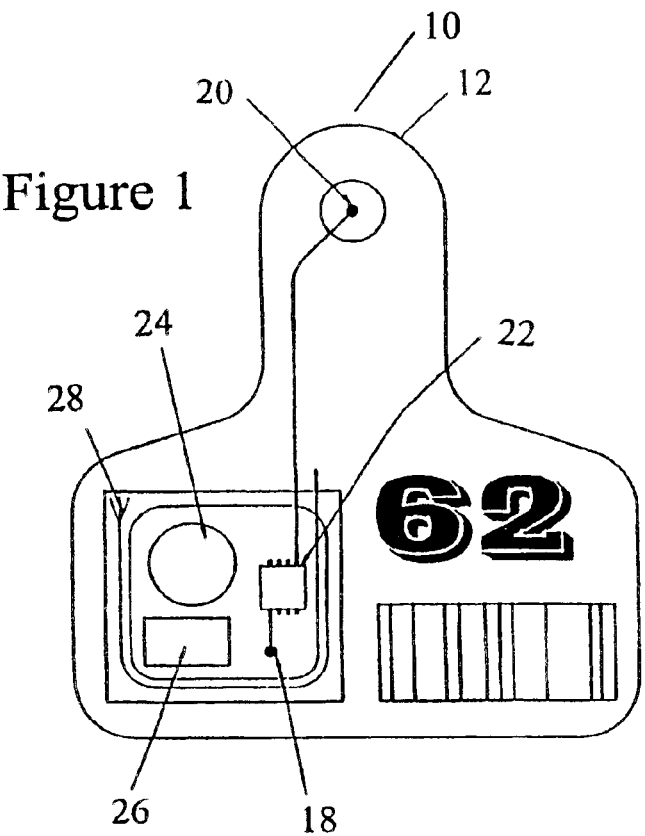
FIG. 1 is a diagrammatic view of an embodiment of a temperature sensing device of the present invention from the inward facing or "animal" side.

As summarised above, the present invention is based upon the applicant's unexpected finding of the correlation between stress, body temperature and variance over time of body temperature, pH and ultimately meat quality in livestock. This finding has important consequences for the agriculture industry generally and the primary meat industry in particular. By identifying stressed animals prior to slaughter, appropriate management techniques can be used to reduce the animals' stress level. This will ensure a higher quality meat product after slaughter.

The applicant's findings also have broader application to methods of predicting or measuring pH levels based on the pH/temperature correlation.

Animal body temperature may be measured using a broad range of temperature sensors including tympanic, rectal, colonic, and skin sensors. Sensors ingested or inserted in bodily canals are not widely used due to the difficulty of inserting them, and because they are easily dislodged or expelled by an animal. Preferably, a skin temperature measurement is taken to avoid these invasive and less desirable alternative techniques. Conveniently, temperature may be measured using a temperature sensing device of the present invention discussed below. However, with temperature measurements from the skin as opposed to the body core, the ambient environmental temperature must be taken into account. The slope of prediction between variance in temperature and ultimate pH of meat shows consistency with temperature change. However, it shifts to the right, or to the left, depending upon the environmental conditions including temperature and solar radiation.

Measures of animal and ambient air temperature or measurements corresponding thereto, and usefully over a predetermined time period are required. On the farm, any time interval, regular or irregular, desired may be selected. Continual on-line monitoring not limited to a specific time period is contemplated. Alternatively, monitoring for selected time periods of hours, days, weeks or even months is feasible.

In the slaughtering context, the correlation between body temperature at slaughter and pH levels of meat are stronger if the measures are integrated for an extended period, which may be up to 2–5 days, but is preferably between 3–36 hrs, more preferably 8–24 hrs and most preferably at least 12–14 hours prior to slaughter.

Within the monitoring period it is preferred that measurements be taken at regular intervals such as hourly, half hourly, every quarter hour, every ten minutes or the like. The preferred regime is no more frequent than every ten minutes.

The applicants have found that skin/body temperature may reflect metabolic activities associated with the stress response. A greater stress response is likely to result in a greater metabolic activation to re-establish the homeostatic norm either through a greater generation of heat and elevation of body temperature or heat loss and a lowering of body temperature. Except in circumstances of pathophysiological heat exhaustion, dehydration or febrile responses these changes are usually short-lived in nature and small in magnitude.

Measurements of animal body-temperature made at discrete points of time during the pre-slaughter period are unlikely to give a representation of the stress experienced cumulatively over the preslaughter period. A single experienced stressor is unlikely to cause meat quality problems whereas cumulative stressor exposure over a period of time, without replenishment, will do so.

Correspondingly, single point temperature measures may well coincide with either a single stressor induced peak or a trough between numerous stressor induced peaks in body temperature, either way unlikely to provide an accurate assessment. It is for this reason that measurements over a time period prior to slaughter are required.

The applicant hypothesised that the best measure of energy used, and by correspondence glycogen depleted from muscles and predicted ultimate pH, would be the variation in body (or skin) temperature over time. The variation will represent both periods in which skin/body temperature has fallen and the required energy consumption to correct, and periods in which body temperature has risen, reflecting increased metabolism and its energy consumption and necessitating heat loss.

A measure of the temperature variation (variance) can be calculated in numerous ways. However, a simple cumulative measure using single measure sample period repeated over the required time is as follows:

find the arithmetic average (x) of all the pooled samples (y1, . . . yn) where I=the first sample variable y and n the last in the sequence, which is also the total number of samples. x=sum(y1+y2+ . . . $y_n$)/n measure and record the variance (v1, . . . vn) of each sample (y1 . . . yn) from this average (x) (i.e. the difference between each sample and the average). Irrespective of whether each sample point is less or more than the average the difference will be indicated as a positive number. v1=x−y1, . . . vn=x−yn.

A further weighting may to be given to each variance dependent upon whether it is above or below the average. Values above the average or mean have energy associated both with generation (variance) and the energy loss through heat transfer needed to return to the average. As such their variance weighting should be greater than those below the average that utilises energy only in returning to the average baseline.

These numbers are then cumulatively added to give a variance score over a predetermined time period. This time period will usually need to be 12 hours or greater to provide meaningful interpretation as to glycogen depletion and energy usage as discussed above. vc=Sum(v1+v2+ . . . vn)

The greater the cumulative score, the greater the energy usage that has occurred and correspondingly the greater the likelihood of both glycogen depletion and subsequent post-slaughter poor meat quality.

To calculate the prediction of meat quality a weighting should also be given to the variance depending upon the environmental conditions. Increasing ambient temperatures are associated with a subtractive weighting, decreasing ambient temperatures with an additive weighting. Solar radiation can also be accommodated for using this method.

The weighting for ambient temperature is approximately ±0.2 pH unit per 3° C. above and below 20° C. (standard weighting of zero).

Based on the applicant's determination of a correlation between temperature and pH, the cumulative effects of variation in body temperature can be manually or electronically correlated with ultimate meat pH using a standard. For example, standardised against a Mettler Toledo pH meter and standards (Mettler Toledo GmbH, Steinbach). Further it could be correlated to any other measure of hydrogen ion concentration, typically using a glass electrode, but other methods including ion selective field effect transistor electrodes could be used. As the increasing pH in meat is correlated with an increase in lactate, a measure of lactate also provides suitable correlation.

The pH level measured can be used as an indicator of an animal's stress level, a pH of greater than 5.8 indicating stress.

Where an animal is found to be stressed, remedial action to lower stress levels can be taken prior to slaughter. A period of feeding should alleviate stress by replenishing glycogen in muscle tissue. This action helps prevent or eliminate post-slaughter meat quality problems.

The methods of the invention may be used in relation to a broad range of animals including domesticated livestock such as sheep, cattle, deer, pigs, chickens, turkeys, ducks, emus, ostriches, rodents, chinchillas and additionally rabbits, possums, goats and the like, as well as the feral counterparts of all of these. Preferred livestock for analysis are sheep, cattle, deer and pigs.

As noted above, the present invention also provides a temperature sensing device depicted generally by the numeral "10" in the accompanying figures. The sensing device (10) is useful in the methods of the invention for measuring temperature. A sensing device (10) of the invention includes a tag represented by the numeral "12". The tag (12) may comprise any of the tags known in the art which can be attached to the skin of an animal, including through the skin, folds thereof, or tissues. Examples of useful tags include ear tags, back tags and tail tags.

Ear tags are conveniently employed.

Figure 2:
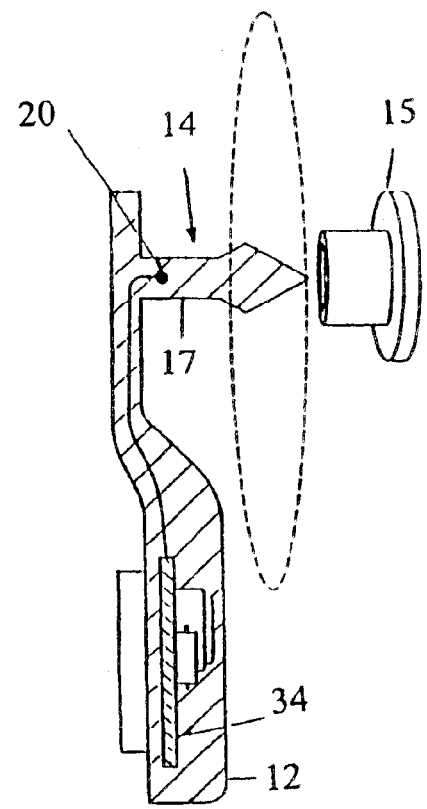
FIG. 2 is a side view of a temperature sensing device of the present invention.

Two part ear tags are disclosed in U.S. Pat. No. 4,854,320 or three part tags of the type disclosed in U.S. Pat. No. 5,675,920 may be used. One part tags wherein an attachment portion of the tag passes over the top of, and back through the ear and tag are also feasible. Currently preferred is a two part tag as illustrated in FIG. 2. For example, the Tru-Test7 perma-flex ear tag (Tru-Test Limited, 241 Ti Rakau Drive, East Tamaki, Auckland, New Zealand). The tags are generally useful for domestic livestock such as sheep, cattle, deer and goats but are not limited thereto.

The tag (12) incorporates at least one attachment portion (14). The attachment portion (14) comprises any suitable attachment means known in the art including any form of skin piercing. The attachment portion (14) may be selected according to the position of attachment on the animal. Suitable attachment portions may include shafts, bands, hooks insertable into or through selected animal tissues, or attachment portions adherable thereto. For example, tags could be superglued to the skin of an animal at a desired location. Preferably, the attachment portion (14) includes a shaft (17) insertable through the ear of an animal. Where necessary backing member(s) (15) may be used to securely fasten the tag to the ear of the animal. The backing member (15) may include a further tag body in some cases. Alternatively, in one embodiment discussed above, the attachment portion (14) may be secured back to the tag (12).

The tag (12) incorporates at least one animal temperature sensor (20) disposed on or in the tag. The sensor (20) is disposed at any location on or in the tag (12) which ensures contact of the sensor (20) with the animal during use. In one embodiment the sensor (20) is in the vicinity of the attachment portion (14). In a preferred embodiment shown in FIG. 2, the sensor (20) is provided on or in the shaft (17) of the attachment portion (14). The location of the sensor (20) in the shaft (17) ensures close contact of the sensor with the animal ear.

The temperature sensor (20) itself may comprise any suitable sensing means known in the art including electronic sensors or thermistors. Temperature sensors suitable for use in the invention are disclosed in U.S. Pat. No. 4,854,328 and U.S. Pat. No. 4,865,044 at least.

As discussed above, where outer body temperature readings, such as skin temperature are used, then the ambient environmental temperature should also be measured. For example, on a hot day an animal's body temperature will rise. If not correlated with air temperature this would falsely indicate a stressed or sick animal. Logically therefore, a more accurate assessment of an animal's body temperature can be made if the ambient air temperature is taken into account.

Accordingly, while a tag (12) without an ambient temperature sensor is contemplated, the tag (12) preferably further includes at least one ambient temperature sensing means (18) provided on the tag (12) at any position suitable for measuring ambient air temperature. Most usually, the ambient temperature sensor (18) will be disposed on or in the side of the tag (12) away from the animal, as shown in FIG. 1. Temperature sensors of the type used for animal temperature measurement may also be employed for ambient temperature measurement. Such other air temperature sensors as are known in the art may also be used.

Correlation of both body and air temperature data can be performed manually by an observer. However, it is preferred that the sensing device (10) further include comparison means for correlating temperature data from both the air and body temperature sensors (18 and 20). Usually, the comparison means will be a microprocessor (22) but application specific electronics could also be implemented.

In order to resolve difficulties associated with heating of the ear tag due to solar radiation, the animal temperature sensor could instead be located some distance from the tag. This is easily done by positioning the body of the tag just inside the ear flap and the sensor just inside the ear canal. The sensor can be located on the end of a flexible wire and glued to the ear. Ambient temperature effects can be minimised by covering the sensor with a small dot of foam insulating tape.

The data output of the body and/or temperature sensor means (18 and 20) may also or alternatively, be sent to remote evaluation means. This will generally require the coupling of the sensor means (18 and 20) to a transmitter. Temperature data as well as animal identification data is transmitted to a remote processor such as a computer. In the case of tagged animals this will permit remote monitoring and checking to be performed, continuously if desired.

In the presently preferred embodiment, the temperature information gathered by both sensors (18 and 20) is relayed to microprocessor (22). In this regard, refer to FIG. 7 which illustrates the circuit diagram for a device according to a slightly modified embodiment. While changes would be required to implement this circuit in the present embodiment the principles of operation are the same. Reference is also made to U.S. Pat. No. 4,854,328, U.S. Pat. No. 4,865,044 and U.S. Pat. No. 3,781,837 which disclose circuitry which could be adapted for this use.

The microprocessor (22) is in turn in responsive communication with indicator means (16). The indicator means (16) may be selected from a broad range of currently known indicators including electronic, visual and acoustic signal generators but are not limited thereto.

In the case of an electronic indicator this may be a device programmed to give out a perceivable signal once a certain predetermined temperature is reached.

In one embodiment, the indicator means (16) may comprise a temperature responsive substance which generates a visual, electromagnetic, electrochemical, or other measurable signal when a predetermined temperature is exceeded. Visual changes such as a change in colour are conveniently employed. Colour change indicators will generally comprise a substance which undergoes a change in state at a precise and predetermined temperature.

In a further embodiment, the indicator means (16) may comprise a plurality of regions, generally less than 10 and preferably less than 5, which undergo a change of state at precise, graduated predetermined temperatures. When colour changes are employed this may usefully result in the graduated change in colour of the indicator from a small portion to substantially the entire indicator. In an embodiment which progressively applies the algorithm resulting in a progressively increasing cumulative value, this progressive colour change might effectively indicate the progressively increasing cumulative value. Alternatively, the colour change might be simply representative of increasing animal temperature. Alternatives include a "traffic light" indicator which, for example, changes from green, to amber, and finally to red as the threshold is exceeded. Other possibilities include opaque materials becoming transparent or translucent to reveal underlying colours as the cumulative value increases or the temperature changes.

The indicators may undergo irreversible changes, especially when continuous monitoring is not contemplated.

Further visual indicator means (16) include, for example, LEDs or flashing lights. Alternatively, audible alarms may be triggered. Combinations of all such indicator means are also feasible. Also contemplated are outputs readable at remote locations. A wide range of indicator means (16) which may be employed in the invention are disclosed in the following US patents: U.S. Pat. No. 3,781,837, U.S. Pat. No. 4,865,044, U.S. Pat. No. 4,854,328 and U.S. Pat. No. 5,675,920 amongst others.

Depending on the types of sensors, indicator and comparison means employed, the sensor device may require a power source. While solar powered devices are contemplated, at least one battery will usually be incorporated into the sensing device (10). In the preferred embodiment depicted in FIG. 1, a battery "24" is employed. A wide variety of batteries (24) are currently available and suitable for use in the ear tag (12).

Where batteries (24) are employed as a power source it is important to identify when a battery (24) has malfunctioned or expired. An indicator showing when the power source has failed would therefore be useful. An appropriate indicator is identified by the numeral "26" in FIG. 1. As with the sensing means, useful indicators include electronic, audio and visual signals as discussed above. For example, when the battery has failed an audible signal could be emitted, driven by a small backup power source. Preferably however, the signal is a visual colour change signal, or extinction of an "OK" LED signal. The colour change may be signalled as an alternative to the temperature colour change signal, or in addition to it provided that the colour changes are distinctive.

The tag (12) may further incorporate communication means. The communication may comprise the export of data and/or for the import of energy. Accordingly, uni- and bi-directional communication means are contemplated. Suitable communication means are identified in the US patents referenced above. They include at least one transmitter and/or antenna but are not limited thereto. In a preferred embodiment of the present invention an antenna (28) is included in the tag (12). The antenna (28) preferably allows bi-directional data communication with the tag (12).

In one use, the antenna (28) provides a means of recharging the battery (24) by use of electromagnetic radiation or an externally applied radio frequency field. In a further use, the antenna (28) permits export of data for logging purposes. Communication may be to remote data logging means to facilitate off-site monitoring of animals. Exported data signals may also provide information relating to the identification number of the animal.

Figure 3:
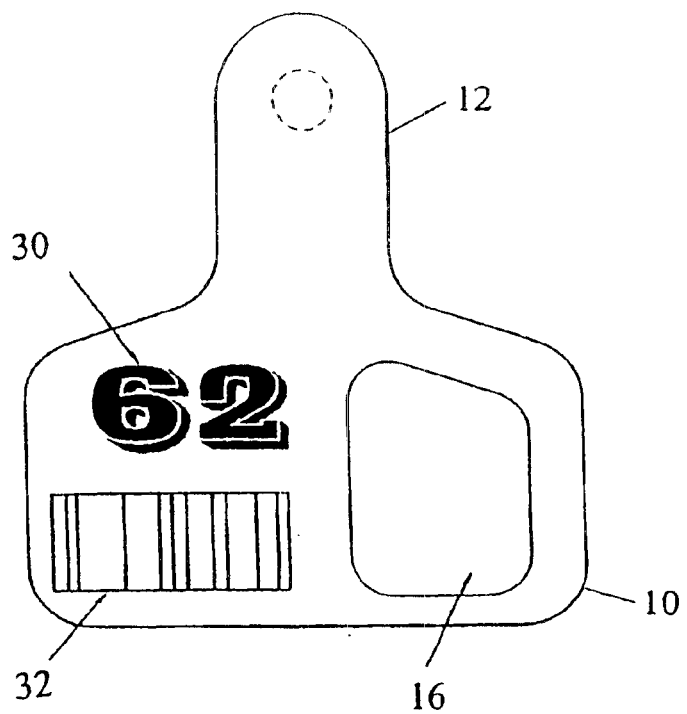
FIG. 3 is a diagrammatic view of an embodiment of a temperature sensing device of the present invention from the outward facing or "environment" side.

It is also customary for tags (12) to include animal identification means. In a simple form this may comprise a unique visual identification means such as a symbol, colour or pattern. Preferably, the visual ID comprises an alphamerical number (30) as shown in FIG. 3. Alternate identification means include electronic identifications, or electronically readable signals which uniquely identify a given animal. Any such electronic signals which are known in the art may be used. One embodiment preferred is the inclusion of a barcode (32) on the tag (12) as shown in FIG. 3. This facilitates scanning of the tag (12) and correlation of data with pre-existing information for the uniquely identified animal. Specific identification systems can also assist in discouraging theft of stock.

The electronic componentry of the ear tag (12) comprising any of all of the antenna (28), battery (24), battery indicator (26) and microprocessor (22) may be provided on or in the tag (12) conveniently on a circuit board (34). Preferably, the componentry is provided within the tag (12) to prevent damage. This may be achieved by covering the componentry once fixed on the tag (12). The cover may be permanently fixed in place or can be releasable. A releasable cover would allow for battery replacement. If the cover is fixed, this may be achieved by gluing, plastic welding or other known fastening means.

Conveniently, the tag (12) is a one piece moulded body.

In a preferred form the tag (12) comprises an integrally moulded body with the componentry sealed therein.

In use, the temperature sensors (18 and 20) of the ear tag (12) will collect temperature data which is communicated to the microprocessor (22) to perform the necessary cumulative algorithms discussed above.

If the outcome of the calculation is a temperature threshold value that indicates a pH of poor quality (greater than 6.2) then a power surge is directed to the indicator to cause an electronic, visual or audible change. The livestock owner or manager can then take steps to reduce the stress level in the animal through appropriate feeding regimes.

High temperature readings may also indicate infected or otherwise unhealthy animals. For pathophysiological measurement either a spike or chronic rise in body temperature can be an important diagnostic tool of disease while longer term tracking can show whether therapeutic treatment of the disease is effective. The tags can therefore serve the dual purpose of signalling the state of health of the animal apart from stress responses. In related applications, the tags can be used in monitoring the status of other processes in animals which at some point are characterised by temperature changes. An example of this is measurement of hormone changes or cycles such as oestrous in an animal.

The useable lifetime of the tag is approximately one month. The lifespan of the tag can be extended through the incorporation of a battery (24) able to be recharged by electromagnetic radiation or radio frequency in the field. Accordingly, both disposable single measure tags (12) and reusable tags (12) are contemplated herein. Disposable tags (12) may be particularly appropriate for short term use in the pre-slaughter period. Custom electronics could greatly increase this lifetime. Once tag identification of a problem occurred, an electronic ID associated with the tag could activate automatic drafting of the animal from a group for remedial action.

Figure 7:
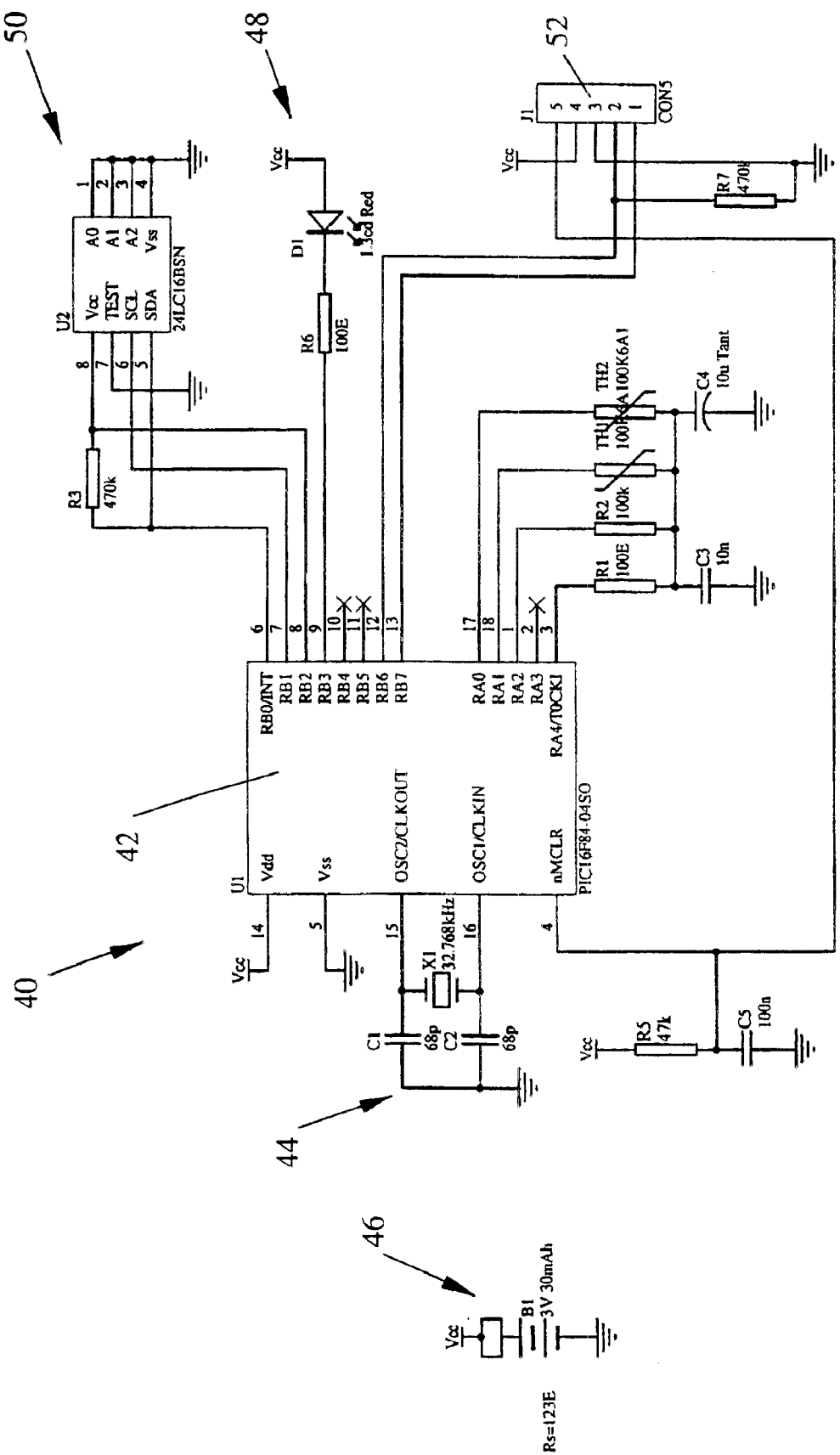
FIG. 7 is a circuit diagram of a circuit which may be implemented in a temperature sensing device which is slightly modified from the device shown in FIGS. 1 to 3.

FIG. 7 is a circuit diagram of a circuit (40) appropriate for use in a tag such as that illustrated in FIGS. 1 to 3, except without the antenna (28).

At the heart of the circuit is microprocessor 42) which receives imputs from ear temperature sensor TH2 and ambient temperature sensor TH1. The microprocessor (42) implements an algorithm which cumulatively takes account of temperature variations in an animal over time. Simple algorithms integrating variations from a mean body temperature over time have been described above. Also described below is a more sophisticated algorithm which may be implemented by microprocessor (42). As an additional input to the microprocessor (42), there is provided a clock (44) which controls the sampling interval at which the microprocessor (42) receives temperature readings from thermisters TH1 and TH2.

The circuit (40) is driven by battery (46) which provides power to the circuit for up to six weeks. A lamp 48 such as LED D1 may flash at intermittent intervals, say every 5 to 10 seconds, to indicate that the circuit is operating. The LED D1 may also be used to provide an indication when the output of the algorithm is such as to exceed a predetermined threshold. In that case, the LED may flash frequently, say every 1 second. This will attract the attendant's attention so that the stressed animals will not be put to immediate slaughter but instead rested and revived as required.

The circuit (40) also includes an optional memory unit (50) which can store up to 4,000 temperature measurements. This will be implemented if the tag is to be used as a diagnostic tool. The data stored in the memory unit (50) may be uploaded via the optional interface (52).

A more sophisticated algorithm for obtaining a cumulative measure of temperature variations in an animal will now be described.

Variable Definitions:

Let $t_{ear}$ be the instantaneous ear temperature

Let $t_{ambient}$ be the instantaneous ambient air temperature d is the difference between ear and ambient temperatures fast is the fast-response filter element slow is the slow response filter element v is the integral of the difference between the two filter elements $c_1$ is the time constant of the fast filter. The time constants are selected according to sampling interval time and threshold detection level.

$c_2$ is the time constant of the slow filter

Time constants are such that $c_1 > c_2$, $0 < c_1 < 1$, $0 > c_2 < 1$ n is the count for the sampling time interval Initialise:

n=1

$d_0 = t_{ear} - t_{ambient}$ $fast_0 = d_0$ $slow_0 = d_0$ $V_0 = 0$

At each sampling time interval:

$d_n = t_{ear} - t_{ambient}$ $fast_n = (1-c_1)*fast_{n-1} + c_1*d_n$ $slow_n = (1-c_2)*slow_{n-1} + c_2*d_n$ $V_n = V_n + (fast_n - slow_n)$ The microprocessor is programmed to repeat the algorithm regularly at each sampling interval until a predetermined time period has elapsed. If at any time during this predetermined time period $v_n$ exceeds a predetermined threshold then the animal is taken to be stressed and lamp (48) of circuit (40) will flash frequently to provide appropriate indication to the attendant. The timer will reset and remain at 0 until v falls below the threshold, at which point the timer will start counting for a predetermined animal withholding period, the timer will again be set to zero. In this way it is ensured that the animal effectively recovers from stress, prior to slaughter.

If, at the elapse of the predetermined time period $v_n$ is less than the threshold then the animal is taken to be within acceptable cumulative stress limits. The lamp (48) may provide an indication that the threshold has not been exceeded.

In the above described algorithm, the entire history of temperature readings is not required, only the most recent reading. Thus, the algorithm requires only three storage locations to be preserved between time steps.

The use of the filter elements removes any dependence on absolute reference temperatures and the need to calibrate the temperature sensors. The filter elements detect trends rather than absolute temperature values.

The filter elements are more resistant to the effects of measurement noise than simple threshold detection.

Figure 8:
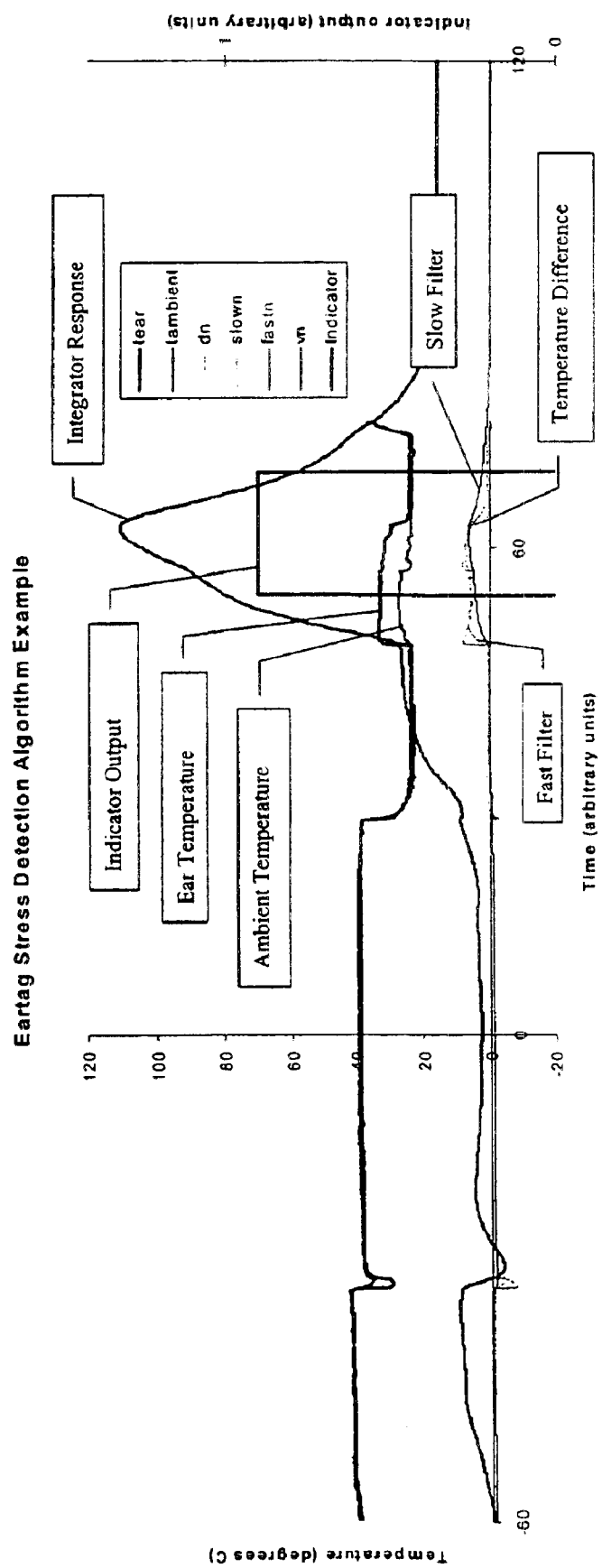
FIG. 8 is a graph plotting temperature readings and the output of a preferred algorithm in accordance with a preferred embodiment of the present invention.

FIG. 8 illustrates an example for the particular algorithm described above. Note that the threshold detection is immune to base line shifts or small spikes in the data. Instead, a long consistent temperature rise is required for detection. The algorithm thus effectively models the rise in body temperature due to stress.

Non-limiting examples illustrating the invention will now be provided.

EXAMPLE 1

Data were obtained in the following manner:

Three groups of twenty prime bulls (18 months of age) were exposed to periods of stressful handling during a 24 hour period lead up period to slaughter.

During this time skin temperature from the ear of each individual animals was measured every 10 minutes. From this an average was calculated and the cumulative variance measured by adding each individual measure difference from the average.

Cumulative variances were then plotted against individual ultimate pH values obtained post-slaughter from meat. Variance values against a set ultimate pH value are presented as an average and standard deviation.

Each group of animals was exposed to a different controlled ambient temperature of 16, 20 or 24 degrees Celsius for the trial period.

In each case the correlation coefficient $r^2$ was greater than 0.90 for variance in temperature predicting ultimate pH of meat.

Figure 4:
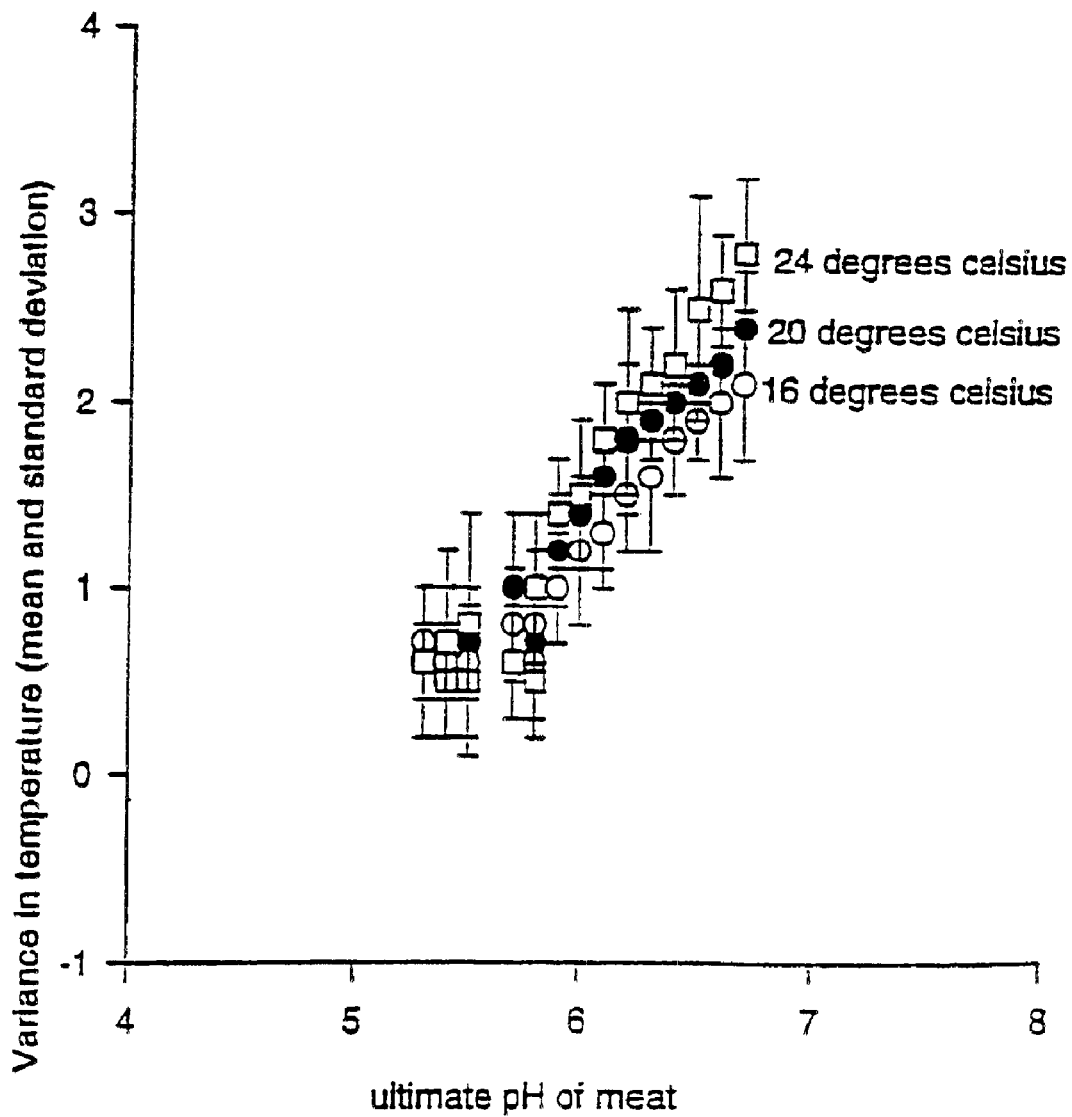
FIG. 4 is a graph plotting the ultimate pH of meat with temperature variance from Example 1.

FIG. 4 presents data for the relationship between variance in temperature and ultimate pH of the meat. Note that below a pH of 6.0 no clear relationship exists. As depicted, variance in body temperature predicts only a pH above 6.0.

For ultimate pH prediction an equation can be calculated to provide an algorithm combining the cumulated variance and the environment temperature.

EXAMPLE 2

20 Adult sheep were subjected to various stressors including rounding up, lairage and transport in the 24 hours prior to slaughter. Ear skin measurements were made during this time, every 15 minutes. For each animal, measurements were averaged over the 24 hours and then for each measured point a variance from mean score was given using degrees celsius above or below the mean.

Figure 5:
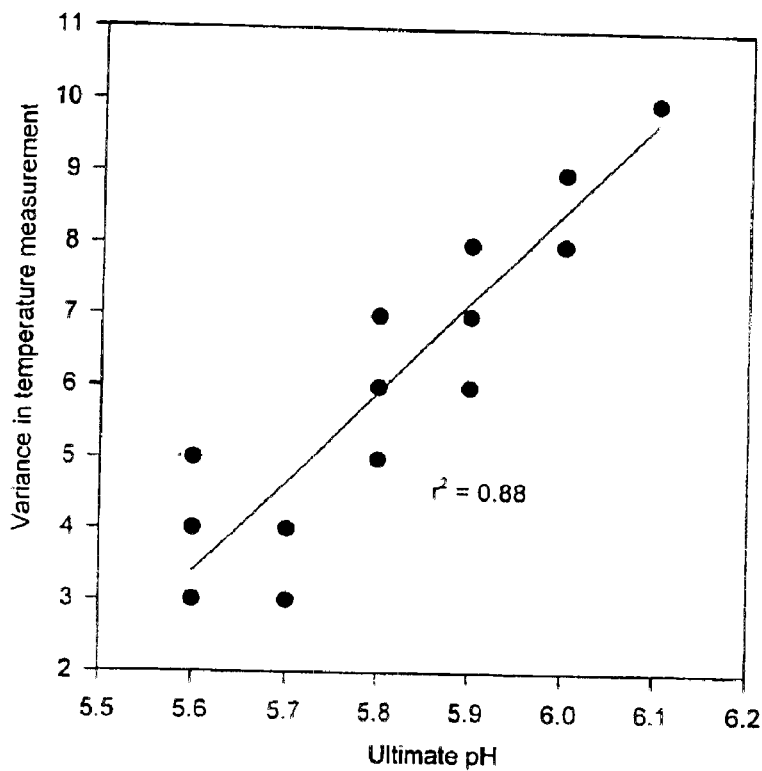
FIG. 5 is a graph plotting the results of Example 2, correlating variance in skin temperature around a mean value over 24 hours in sheep with ultimate pH.

The greatest total individual variance was ranked numerically as 10 and the others normalised as a dividend of this. These variances were then correlated with the ultimate pH obtained from the meat of the slaughtered animals. The results are shown in FIG. 5 which shows relationship of variance in skin temperature around a mean value over 24 hours in sheep correlated against their ultimate pH. The correlation coefficient is displayed. This data suggests that in sheep, as for cattle, measurement of variation in skin or body temperature over a period prior to slaughter can predict the ultimate meat quality.

EXAMPLE 3

A group (14) of adult sheep being monitored developed respiratory and parasitic infections. Monitored ear skin temperatures showed good correlation (correlation coefficient of 0.81) with rectal temperatures in terms of fever peaks and return to normal body temperatures with treatment.

Figure 6:
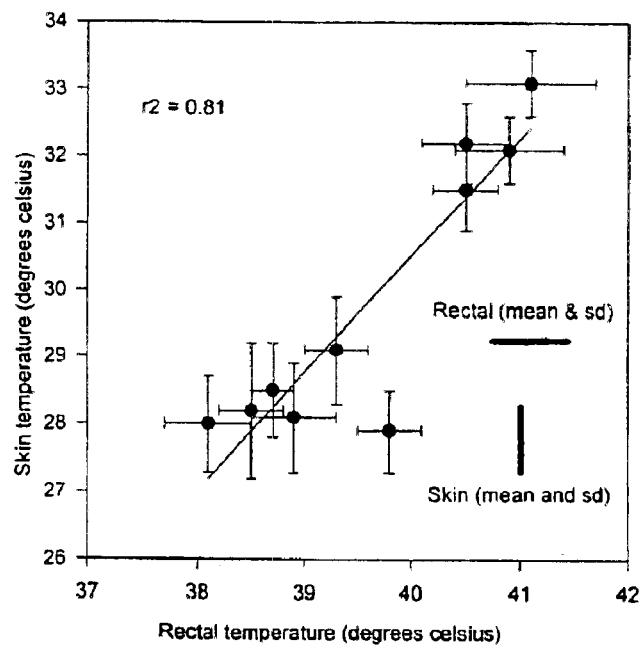
FIG. 6 is a graph plotting the results of Example 3 showing the mean and SD rectal temperatures of adult sheep with similar levels of infection taken at the same time each day at the same ambient temperature. The ear skin temperatures are plotted against corresponding the rectal temperatures.

The data plotted in FIG. 6 supports the notion that ear skin or ear canal temperature can be used to measure pathophysiological states that have accompanying febrile symptoms and recovery from these states.

It will be appreciated that the above description is provided by way of example only and that variations in both the materials and techniques used which are known to those persons skilled in the art are contemplated.

REFERENCES

[1] Cook, C. J. and Devine C. E. (1990) From farm paddock to slaughter floor: a conundrum of biochemical and physiological effects that influence meat quality. AGMARDT Beef Industry Research Development Conference. NZMPB.

[2] Purchas, R. W. (1990) An assessment of the role of pH differences in determining the relative tenderness of meat from bulls and steers. Meat Sciences 27, 129–140.

[3] Watanabe, A., Daly, C. C. and Devine C. E. (1995) The effects of ultimate pH of meat on the tenderness changes during ageing. Meat Science 42, 67–78.

[4] Jacobson, L. H. and Cook, C. J. (1997) The effect of pre-transport cattle management on stress, metabolism and carcass weight of bulls. In: Proceedings of the 43rd International Congress on Meat Science and Technology. Auckland, NZ, pp302–303.

[5] Jacobson, L. H., Cook, C. J., Hodgetts, B. V. and Dean, J. M. The effect of pre-transport on on-farm holding and supplementary feeding, on welfare and meat characteristics of bulls subsequently transported for slaughter. September 1997. (Funding Milestone, MRDC).

[A] Devine C. E. and Chrystall, B. B, (1992) Meat Science, in encyclopedia of Food Science and Technology, ed Hui, Y. H., WileyInterscience, John Wiley and Sons, Inc., New York 17081723.

[B] Devine C. E. and Chrystall, B. B. (1989) High ultimate pH in sheep in Darkcuttinu in cattle and sheep. Proceedings of an Australian Workshop. Pp 5565 Ed. S. U. Fabiansson, W. R. Shorthose and R. D. Warner AMLRDC, Sydney Australia.

[C] Devine C. D. Graafhuis, A. E. Muir, P. D. and Chrystall, B. B. (1994) The effect of growth rate and ultimate pH on meat quality of lambs. Meat Sci. 36 143–150

All US references cited in the text of this specification are incorporated herein by reference.

What is claimed is:

1. A method of providing an indication of at least one of meat quality, pH levels, and stress levels in an animal, the method comprising:

obtaining measurements corresponding to a body temperature of the animal at periodic sampling intervals over a predetermined time period;

determining an indicator or measure of the sum total extent of all of the variation in said measurements over said time period; and comparing said indicator or measure of the sum total extent of all of the variation to a predetermined threshold to determine the indication.

2. The method as claimed in claim 1 wherein ten or more measurements corresponding to body temperature are taken.

3. The method as claimed in claim 1 wherein the predetermined time period is at least 12 hours.

4. The method as claimed in claim 1 wherein the predetermined time period extends up to 24 hours.

5. The method as claimed in claim 1 wherein the indication or measure of the extent of variation algorithm is applied at a end of the predetermined time period.

6. The method as claimed in claim 1 wherein the indication or measure of the extend of variation is applied progressively.

7. The method as claimed in claim 6 wherein said comparing is conducted after each application of the algorithm.

8. The method as claimed in claim 6 wherein the indication or measure of the extent of variation is applied progressively as each measurement corresponding to body temperature is taken.

9. The method as claimed in claim 1 further comprising, in the event of the threshold being exceeded, providing an indication of the threshold being exceeded.

10. The method as claimed in claim 9 further including setting the animal aside for a predetermined animal withholding period in the event of the threshold being exceeded.

11. The method as claimed in claim 1 wherein the determining said indication or measure of the extent of variation comprises:

where:
$t_{ear}$ is the instantaneous ear temperature;
$t_{ambient}$ is the instantaneous ambient air temperature;
d is the difference between ear and ambient temperatures;
fast is the fast-response filter element;
slow is the slow response filter element;
v is the integral of the difference between the two filter elements;
$c_1$ is the time constant of the fast filter;
$c_2$ is the time constant of the slow filter;
Time constants are such that $C_1 > c_2$, $0 < c_1 < 1, 0 < c_2 < 1$;
where initially:
n=1
$d_0 = t_{ear} - t_{ambient}$
$fast_0 = d_0$
$slow_0 = d_0$
$v_0 = 0$
and where at each sampling interval:
$d_n = t_{ear} - t_{ambient}$
$fast_n = (1 - c_1) * fast_{n-1} + c_1 * d_n$
$slow_n = (1 - c_2) * slow_{n-1} + c_2 * d_n$
then: $v_n = v_{n-1} + (fast_n - slow_n)$.

12. The method as claimed in claim 1 wherein the measurements are taken on the outer part of the animal's body.

13. The method as claimed in claim 12 wherein skin temperature measurements are taken and compensation is provided for at least ambient temperature or solar radiation.

14. The method as claimed in claim 12 wherein measurements are taken in the ear canal of the animal.

15. A method of providing an indication of at least one of meat quality, pH levels, and stress levels in an animal, the method comprising:
a) obtaining measurements corresponding to a body temperature of the animal at periodic sampling intervals;
b) applying an algorithm to the measurements obtained from a), which algorithm cumulatively takes account of variations in body temperature over time; and
c) correlating the results of the algorithm with at least one of a meat tenderness, a pH, and a stress standard.

16. The method as claimed in claim 15 wherein a mean is calculated progressively as each measurement corresponding to temperature is taken.

17. A system for providing an indication of at least one of meat quality, pH levels, and stress levels in an animal to be slaughtered, the system comprising:
a body mountable measurement device for obtaining measurements corresponding to the body temperature of the animal at periodic sampling intervals over a period of between 3–36 hours; and
a processor or controller configured to:
receive said measurements from said measurement device;
determine an indicator or measure of the sum total extent of all of the variation in said measurements over said period;
compare said indicator or measure of the sum total extent of all of the variation to a predetermined threshold to obtain a result; and
providing said result of said comparison as output.

18. The system as claimed in claim 17 wherein said processor further configured to:
determine the animal's mean body temperature from the measurements;
calculate the variance between each measurement and the mean; and
add all variances to obtain a cumulative variance score.

19. The system as claimed in claim 17 wherein the algorithm comprises the following the indication or measure of the extent of variation is determined:

where:
$t_{ear}$ is the instantaneous ear temperature;
$t_{ambient}$ is the instantaneous ambient air temperature;
d is the difference between ear and ambient temperatures;
fast is the fast-response filter element;
slow is the slow response filter element;
v is the integral of the difference between the two filter elements;
$c_1$ is the time constant of the fast filter;
$c_2$ is the time constant of the slow filter;
Time constants are such that $C_1 > c_2$, $0 < c_1 < 1, 0 < c_2 < 1$;
where initially:
n=1
$d_0 = t_{ear} - t_{ambient}$
$fast_0 = d_0$
$slow_0 = d_0$
$V_0 = 0$
and where at each sampling interval:
$d_n = t_{ear} - t_{ambient}$
$fast_n = (1 - c_1) * fast_{n-1} + c_1 * d_n$
$slow_n = (1 - c_2) * slow_{n-1} + c_2 * d_n$
then: $v_n = v_{n-1} + (fast_n - slow_n)$.

20. The system as claimed in claim 17 wherein the system: is embodied in an all-in-one indicator device.

21. The system as claimed in claim 20 wherein the device is provided in the form of an ear tag.

22. The system as claimed in claim 21 wherein the tag incorporates the measurement device.

23. The system as claimed in claim 17 wherein the processor is provided by way of a remote computer.

24. The system as claimed in claim 17 wherein the processor is adapted to output a numeric value from a comparison with a meat tenderness scale.

25. The system as claimed in claim 17 wherein the processor is operable to compare the output of the algorithm to a predetermined threshold.

26. The system as claimed in claim 25 further including an indicator to indicate where the output of the algorithm has exceeded the predetermined threshold.

27. The system as claimed in claim 26 wherein the indicator is also operable to provide an indication that the system is functioning.

28. A temperature sensing device comprising:
- a tag having an attachment portion to extend through a body part of an animal;
- one or more animal temperature sensors disposed on/in the attachment portion for contact with the animal during use and providing an output indicative of temperature; and
- an indicator mounted on the tag or incorporated therewith and communicating with the one or more animal temperature sensors, said indicator being configured to provide a local indication depending on said output from said one or more animal temperature sensors.

29. The tag as claimed in claim 28 wherein the tag is an ear tag.

30. The tag as claimed in claim 28 wherein an ambient temperature sensor is also provided on the tag.

31. The tag as claimed in claim 28 wherein comparison means is provided for comparing the ambient temperature with the animal temperature.

32. The tag as claimed in claim 31 wherein the indicator is disposed on the tag, the indicator being responsive to the comparison means.

33. The tag as claimed in claim 28 wherein the tag comprises a one piece molded body.

34. A method of providing an indication of at least one of meat quality, pH levels, and stress levels in an animal, the method comprising:
- obtaining measurements corresponding to the body temperature of the animal at periodic sampling intervals;
- determining that animal' mean body temperature reading over the predetermined time period; calculating the variance between each measurement and the mean determined; and
- adding all variances to obtain a cumulative temperature variance score,
- comparing said score to a predetermined threshold.

35. The method as claimed in claim 34 wherein the variance is calculated progressively.

36. The method as claimed in claim 35 wherein the variance is calculated progressively as each measurement corresponding to body temperature is taken.

37. The method as claimed in claim 35 wherein the comparison is conducted after each application of the algorithm.

38. A method of providing an indication of at least one of meat quality, pH levels, and stress levels in an animal, the method comprising:
- obtaining measurements corresponding to the body temperature of the animal at periodic sampling intervals;
- calculating progressively a mean as each measurement corresponding to temperature is taken;
- applying an algorithm to the measurements which cumulatively takes account of variations in body temperature over time; and
- comparing the results of said algorithm to a predetermined threshold.

39. A method of providing an indication of at least one of meat quality, pH levels, and stress levels in an animal, the method comprising:
- obtaining measurements corresponding to the body temperature of the animal at periodic sampling intervals;
- applying an algorithm where:

$t_{ear}$ is the instantaneous ear temperature;

$t_{ambient}$ is the instantaneous ambient air temperature;

d is the difference between ear and ambient temperatures;

fast is the fast-response filter element;

slow is the slow response filter element;

v is the integral of the difference between the two filter elements;

$C_1$ is the time constant of the fast filter; °

$c_2$ is the time constant of the slow filter;

Time constants are such that $c_1 > C_2$, $0 < c_1 < 1, 0 < C_{2 < 1}$;

where initially:

n=1

$d_0 = t_{ear} - t_{ambient}$ $fast_0 = d_0$ $slow_0 = d_0$ $V_0 = 0$ and where at each sampling interval:

$d_n = t_{ear} - t_{ambient}$ $fast_n = (1-c_1)*fast_{n-1} + c_1*d_n$ $slow_n = (1-c_2)*slow_{n-1} + c_2*d_n$ then: $V_n = V_{n-1} + (fast_n - slow_n)$; and comparing vn to a predetermined threshold.

40. A system for providing an indication of at least one of meat quality, pH levels, and stress levels in an animal to be slaughtered, the system comprising:
- a body mountable measurement device for obtaining measurements corresponding to the body temperature of the animal at periodic sampling intervals over a period of between 336 hours; and
- a processor having an input means for receiving the measurements from the measurement device, the processor operable to:
- determine the animal's mean body temperature from the measurements;
- calculate the variance between each measurement and the mean; and
- add all variances to obtain a cumulative variance score;
- wherein the processor has an output means for providing the cumulative variance score.

41. A system for providing an indication of at least one of meat quality, pH levels, and stress levels in an animal to be slaughtered, the system comprising:
- a body mountable measurement device for obtaining measurements corresponding to the body temperature of the animal at periodic sampling intervals over a period of between 336 hours; and
- a processor having an input means for receiving the measurements from the measurement device, the processor operable to implement an algorithm where:

$t_{ear}$ is the instantaneous ear temperature;

$t_{ambient}$ is the instantaneous ambient air temperature;

d is the difference between ear and ambient temperatures;

fast is the fast-response filter element;

slow is the slow response filter element;

v is the integral of the difference between the two filter elements;

$c_1$ is the time constant of the fast filter;

$c_2$ is the time constant of the slow filter;

Time constants are such that $c_1 > c_2$, $0 < c_1 < 1, 0 < c_2 < 1$;

where initially:

n=1
$d_0 = t_{ear} - t_{ambient}$
$fast_0 = d_0$
$slow_0 = d_0$
$v_0 = 0$ and where at each sampling interval:

$d_n = t_{ear} - t_{ambient}$
$fast_n = (1-c_1)*fast_{n-1} + c_1*d_n$
$slow_n = (1-c_2*slow_{n-1} + c_2*d_n$ then: $V_n = V_{n-1} + fast_n - slow_n)$ wherein the processor has an output means for providing the result $v_n$.

42. A system for providing an indication of at least one of meat quality, pH levels, and stress levels in an animal to be slaughtered, the system comprising:

a body mountable measurement device for obtaining measurements corresponding to the body temperature of the animal at periodic sampling intervals over a period of between 336 hours; and a processor having an input means for receiving the measurements from the measurement device, the processor operable to implement an algorithm to the measurements, which algorithm cumulatively takes account of variations in body temperature over a time window, wherein the processor has an output means for providing the result of the algorithm;

wherein the system is embodied in an all-in-one indicator device.

43. The system as claimed in claim 42 wherein the device is provided in the form of an ear tag.

44. The system as claimed in claim 43 wherein the tag incorporates the measurement device.

45. A system for providing an indication of at least one of meat quality, pH levels, and stress levels in an animal to be slaughtered, the system comprising:

a body mountable measurement device for obtaining measurements corresponding to the body temperature of the animal at periodic sampling intervals over a period of between 336 hours; and a processor having an input means for receiving the measurements from the measurement device, the processor operable to implement an algorithm to the measurements, which algorithm cumulatively takes account of variations in body temperature over a time window, wherein the processor has an output adapted to output a numeric value result of the algorithm from a comparison with a meat tenderness scale.

46. A system for providing an indication of at least one of meat quality, pH levels, and stress levels in an animal to be slaughtered, the system comprising:

a body mountable measurement device for obtaining measurements corresponding to the body temperature of the animal at periodic sampling intervals over a period of between 336 hours; and a processor having an input means for receiving the measurements from the measurement device, the processor operable to implement an algorithm to the measurements, which algorithm cumulatively takes account of variations in body temperature over a time window, and operable to compare the output of the algorithm to a predetermined threshold wherein the processor has an output means for providing the result of the algorithm;

an indicator to indicate where the output of the algorithm has exceeded the predetermined threshold and provide an indication that the system is functioning.

47. A temperature sensing device including:

a tag having an attachment portion to extend through a body part of an animal, the tag incorporating an indicator means;

one or more animal temperature sensors disposed on/in the attachment portion for contact with the animal during use;

an ambient temperature sensor provided on the tag; comparison means is provided to compare the ambient temperature with the animal temperature;

an indicator is disposed on the tag, the indicator being responsive to the comparison means.

* * * * *

UNITED STATES PATENT AND TRADEMARK OFFICE
CERTIFICATE OF CORRECTION

PATENT NO. : 6,862,550 B1
DATED : March 1, 2005
INVENTOR(S) : Christian John Cook It is certified that error appears in the above-identified patent and that said Letters Patent is hereby corrected as shown below:

Title page,
Item [57], ABSTRACT,
Line 11, change "per-determined" to -- predetermined --.

Column 1,
Line 21, change "PH" to -- pH --.

Column 3,
Line 26, change "measurements" to -- measurement --.

Column 4,
Line 44, change "compound" to -- compared --.

Column 7,
Line 5, remove "100".
Line 45, before "rectal" remove "the".

Column 9,
Line 6, change "I=the" to -- 1=the --.

Column 10,
Line 12, change "4,854,320" to -- 4,854,328 --.

Column 13,
Line 6, after "any" change "of" to -- or --.
Line 55, change "42)" to -- (42) --.
Line 56, change "imputs" to -- inputs --.

Column 14,
Line 40, change "$V_0=0$" to -- $v_0=0$ --.
Line 46, change "$V_n=V_n+(fast_n-slow_n)$" to -- $v_n=v_{n-1}+(fast_n-slow_n)$ --.

Column 17,
Line 4, remove "algorithm".
Line 7, change "extend" to -- extent --.
Line 35, change "$C_1>c_2$" to -- $c_1>c_2$ --.
Line 46, change "$v_n=V_{n-1}+(fast_n-slow_n)$" to -- $v_n=v_{n-1}+(fast_n-slow_n)$ --.

UNITED STATES PATENT AND TRADEMARK OFFICE
CERTIFICATE OF CORRECTION

PATENT NO. : 6,862,550 B1
DATED : March 1, 2005
INVENTOR(S) : Christian John Cook It is certified that error appears in the above-identified patent and that said Letters Patent is hereby corrected as shown below:

Column 18,
Lines 25-26, remove "the algorithm comprises the following".
Line 39, change "$C_1 > c_2$" to -- $c_1 > c_2$ --.
Line 43, change "$_{fast0} = d_0$" to -- $fast_0 = d_0$ --.
Line 44, change "$_{slow0} = d_0$" to -- $slow_0 = d_0$ --.
Line 45, change "$V_0 = 0$" to -- $v_0 = 0$ --.
Line 52, change "system:" to -- system --.

Column 19,
Line 34, change "animal'" to -- animal's --.
Lines 34-39, change the formatting to
    -- determining that animal's mean body temperature
        reading over the predetermined time period;
      calculating the variance between each measurement and
        the mean determined; and
      adding all variances to obtain a cumulative temperature
        variance score, comparing said score to a
        predetermined threshold. --.

Column 20,
Line 9, change "$C_1$" to -- $c_1$ --.
Line 9, remove "°".
Line 11, change "$c_1 > C_2$" to -- $c_1 > c_2$ --.
Line 11, change "$0 < C_{2<1;}$" to -- $0 < c_2 < 1$ --.
Line 19, change "$V_0 = 0$" to -- $v_0 = 0$ --.
Line 25, change "$V_n = V_{n-1} + (fast_n - slow_n)$" to -- $v_n = v_{n-1} + (fast_n - slow_n)$ --.
Line 26, change "vn" to -- $v_n$ --.
Lines 33 and 51, change "336" to -- 3-36 --.

Column 21,
Line 10, change "$V_n = V_{n-1} + fast_n - slow_n)$" to -- $v_n = v_{n-1} + (fast_n - slow_n)$ --.
Lines 21 and 42, change "336" to -- 3-36 --.

UNITED STATES PATENT AND TRADEMARK OFFICE
CERTIFICATE OF CORRECTION

PATENT NO. : 6,862,550 B1
DATED : March 1, 2005
INVENTOR(S) : Christian John Cook It is certified that error appears in the above-identified patent and that said Letters Patent is hereby corrected as shown below:

Column 22,
Line 15, change "336" to -- 3-36 --.

Signed and Sealed this

First Day of November, 2005

JON W. DUDAS
*Director of the United States Patent and Trademark Office*